(12) United States Patent
Miller et al.

(10) Patent No.: US 9,862,680 B2
(45) Date of Patent: Jan. 9, 2018

(54) PERIPHERALLY SUBSTITUTED MONOCYCLIC BETA-LACTAMS

(71) Applicant: University of Notre Dame du Lac, Notre Dame, IN (US)

(72) Inventors: Marvin Miller, South Bend, IN (US); Serena Carosso, Mishawaka, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 0 days.

(21) Appl. No.: 15/181,303

(22) Filed: Jun. 13, 2016

(65) Prior Publication Data
US 2017/0355671 A1    Dec. 14, 2017

(51) Int. Cl.
*C07D 205/08*  (2006.01)
*A61K 31/397*  (2006.01)
*C07D 417/12*  (2006.01)

(52) U.S. Cl.
CPC ......... *C07D 205/08* (2013.01); *C07D 417/12* (2013.01)

(58) Field of Classification Search
None
See application file for complete search history.

(56) References Cited

U.S. PATENT DOCUMENTS 5,250,676 A * 10/1993 Gasparski ............ C07D 205/08
540/200

OTHER PUBLICATIONS

Bulychev, et al., Tetrahedron, 56:5719 (2000).*
Bellettini, et al., "Intermolecular Addition of Amines to an N-Tosyloxy beta-Lactam(1)," J Org Chem., 61 (22):7959-7962, Nov. 1996.
Bulychev, et al., "Potent mechanism-based inhibition of the TEM-1 .beta.-lactamase by novel N-sulfonyloxy .beta.-lactams," J. Am. Chem. Soc., 117(22):5938-5943, Jun. 1995.
Fischbach, et al., "Antibiotics for Emerging Pathogens," Science, 325(5944):1089-1093, Aug. 2009.
Fisher, et al., "Bacterial Resistance to Beta-lactam Antibiotics: Compelling Opportunism, Compelling Opportunity," Chem Rev, 105(2):395-424, Feb. 2005.
Horne, et al., "Heterocyclic Peptide Backbone Modifications in an Alpha-helical Coiled Coil," J Am Chem Soc., 126 (47):15366-15367, Dec. 2004.
Kotra, et al., "β-Lactam Antibiotics, β-lactamases and Bacterial Resistance," Bulletin de l'Institut Pasteur, 96 (3):139-150, Jul.-Sep. 1998.
Rajendra, et al., "Intramolecular Electrophilic Additions to Olefins in Organic Syntheses. Stereoselective Synthesis of 3,4-substituted .beta.-lactams by Bromine-induced Oxidative Cyclization of O-acyl .beta.,.gamma.-unsaturated Hydroxamic Acid Derivatives," J. Org. Chem., 52(20):4471-4477, Oct. 1987.
Teng, et al., "Diastereoselective Addition of Nucleophiles to the C3 position of N-(tosyloxy)-.beta.-lactams," J. Am. Chem. Soc., 115(2):548-554, Jan. 1993.
Teng, et al., "β-Lactamase Inhibitors Derived from N-tosyloxy-β-lactams," Bioorg Med Chem, 1(2):,151-154, Aug. 1993.

* cited by examiner

*Primary Examiner* — Michael Barker
(74) *Attorney, Agent, or Firm* — Haukaas Fortius PLLC; Michael H. Haukaas

(57) ABSTRACT

The invention provides monobactams that can be used as antibacterial agents or intermediates for the preparation of other useful compounds such as antibacterial agents.

20 Claims, 1 Drawing Sheet

PERIPHERALLY SUBSTITUTED MONOCYCLIC BETA-LACTAMS

GOVERNMENT SUPPORT

This invention was made with government support under Grant No. 1R21AI098689 awarded by the National Institutes of Health. The government has certain rights in the invention.

CROSS-REFERENCE TO RELATED APPLICATIONS

This application claims the benefit of, and priority to, U.S. Provisional Patent Application Ser. No. 62/174,320, filed Jun. 11, 2015.

BACKGROUND OF THE INVENTION

The clinical introduction of penicillin in the 1940s is a milestone in the history of mankind since it led to a drastic decrease of the mortality rate caused by bacterial infections and also to an unprecedented improvement in the quality of life. The two decades between 1940 and 1960 have been defined as the "golden era of antibiotics" in which several new classes of antibiotics were developed and introduced on the market. Many life-threatening diseases became easily curable and the number of deaths or disabilities due to infectious diseases was drastically decreased. However, over the years bacteria exposed to antibiotics developed a large array of mechanisms of resistance, including modification of the drug target, molecular bypass, active efflux (or decreased entry) and chemical modification of the compound. As a consequence the 20 commonly used antibiotics are becoming less and less effective and the spread of multi-drug resistant bacteria is becoming a major threat for public health. Thus, the need for new antibiotics, with novel structures and/or mechanism of action, becomes more pressing every year.

SUMMARY

The present disclosure generally provides monobactams that can be used as antibacterial agents or as intermediates for the preparation of other compounds such as antibacterial agents.

In one embodiment, the present disclosure provides an N-sulfonyloxy β-lactam compound of Formula (I):

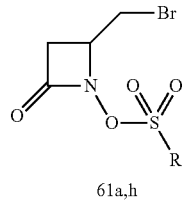

(I)

In some aspects, R can be an optionally substituted aryl, or an optionally substituted alkenyl(aryl), and R can be selected from the group consisting of:

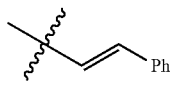
a

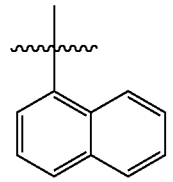
b

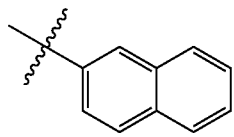
c

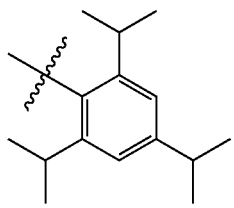
d

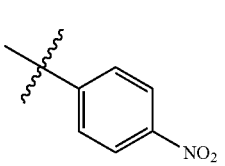
e

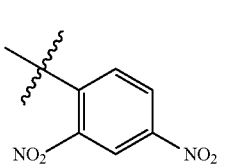
f

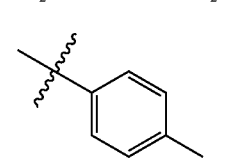
g

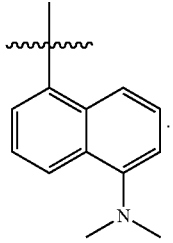
h

In some aspects the present disclosure provides compounds of claim 1 selected from the group consisting of 41, 43, 44, 48:

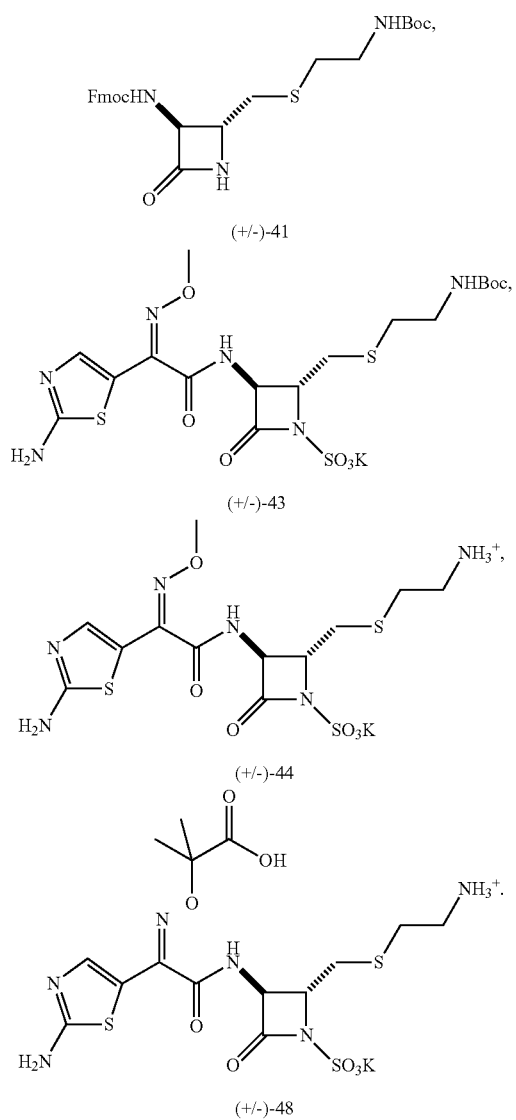

(+/-)-41

(+/-)-43

(+/-)-44

(+/-)-48

The disclosure also provides for pharmaceutically acceptable salts of compounds 41, 43, 44, and 48. The present disclosure provides compounds of claim 1 wherein the monobactam has a sulfur-containing side chain at the C4 position, and wherein the monobactam has an aminothiazole methoxime (ATMO) side chain at the C3 position.

In additional embodiments, the present disclosure provides a method of inhibiting β-lactamase activity comprising contacting a N-sulfonyloxy β-lactam with a β-lactamase enzyme. In some aspects, the β-lactamase enzyme can be a β-lactamase enzyme isolated from a pathogenic bacterium. In some aspects, β-lactamase enzyme can be naturally occurring in a pathogenic bacterium. The pathogenic bacterium can be either a Gram positive bacterium or a Gram negative bacterium. The gram positive bacteria can be selected from the group consisting of *B. subtilis* and *M. vaccae*. Gram negative bacteria can be selected from the group consisting of *A. baumannii*, *P. aeruginosa* and *E. coli*. In additional aspects, the N-sulfonyloxy β-lactam or pharmaceutically acceptable salt thereof has the general Formula (I):

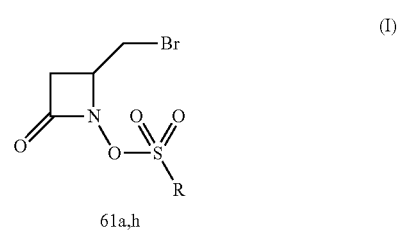

61a,h wherein R can be an optionally substituted aryl, or an optionally substituted alkenyl(aryl). The N-sulfonyloxy β-lactam can be selected from the group consisting of 41, 43, 44, 48 and a pharmaceutically acceptable salt thereof:

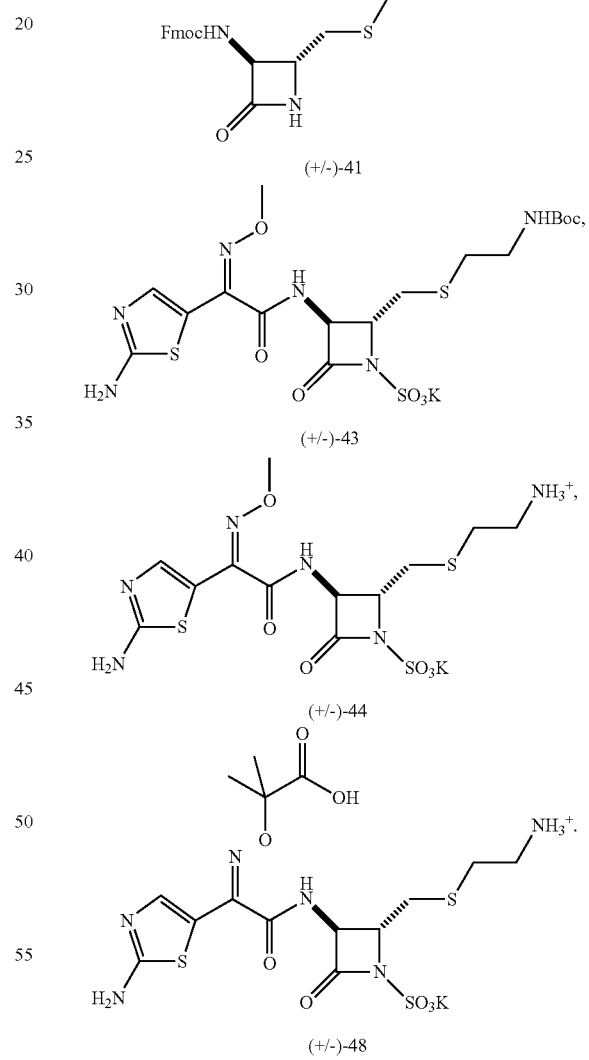

(+/-)-41

(+/-)-43

(+/-)-44

(+/-)-48

In additional embodiments, the present disclosure provides methods of treating a bacterial infection comprising administering to a subject in need thereof an effective antibacterial amount of a N-sulfonyloxy β-lactam or a pharmaceutically acceptable salt thereof. In one aspect, the N-sulfonyloxy β-lactam or pharmaceutically acceptable salt thereof has the general Formula (I):

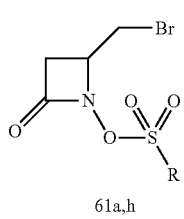

wherein R can be an optionally substituted aryl, or an optionally substituted alkenyl(aryl). In some aspects the N-sulfonyloxy β-lactam can be selected from the group consisting of 41, 43, 44, 48 and a pharmaceutically acceptable salt thereof:

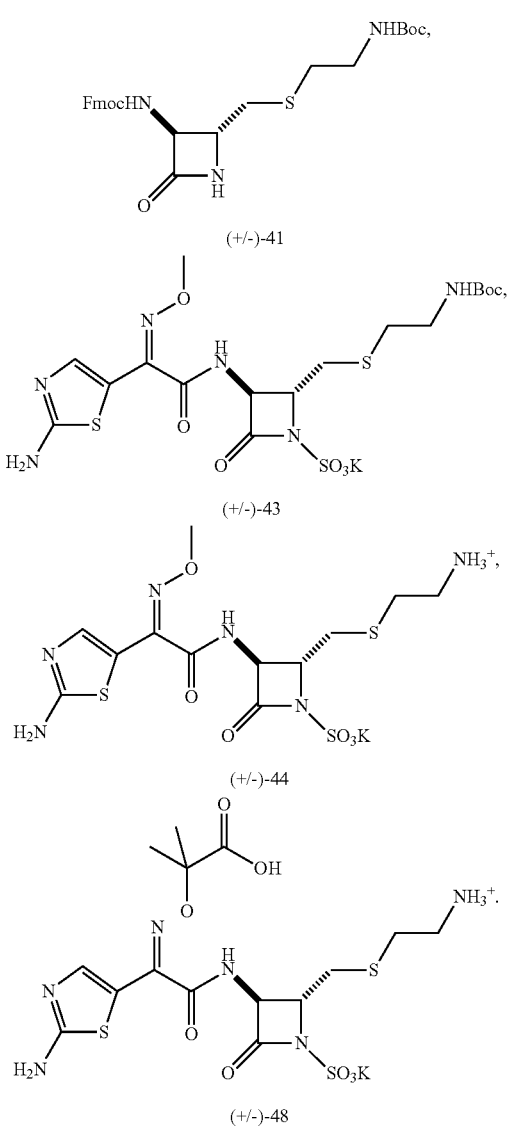

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Monobactams are a class of β-lactam antibiotics that contain a 2-oxoazetidinone-1-sulfonic acid moiety and which are produced by a variety of Gram-negative bacteria. The structure and the absolute configuration of naturally occurring monobactams, as well as their mode of action, has been investigated using total synthesis, which investigations provided important contributions to monobactam research because none of the eight naturally occurring monobactams has proved to be a useful source of material for semi-synthetic modification.

The development of new methodologies for the synthesis of monocyclic β-lactam antibiotics is described herein. In particular, the synthesis of β-lactams that display a sulfur-containing side chain at the C4 position and an ATMO side chain at the C3 position have been described. Several analogs have been generated through a synthetic route in which a bromine induced cyclization is used for the construction of the β-lactam ring. The biological activity of the final compounds has been also evaluated. Efforts have also been directed to the synthesis of monocyclic β-lactams containing an ATMO side chain at the C3 position and/or a 1,2,3-triazole moiety at the C4 position, which is introduced through the use of click chemistry. The biological activity of the final compounds can be evaluated using in-house agar diffusion essays.

Figure 1:
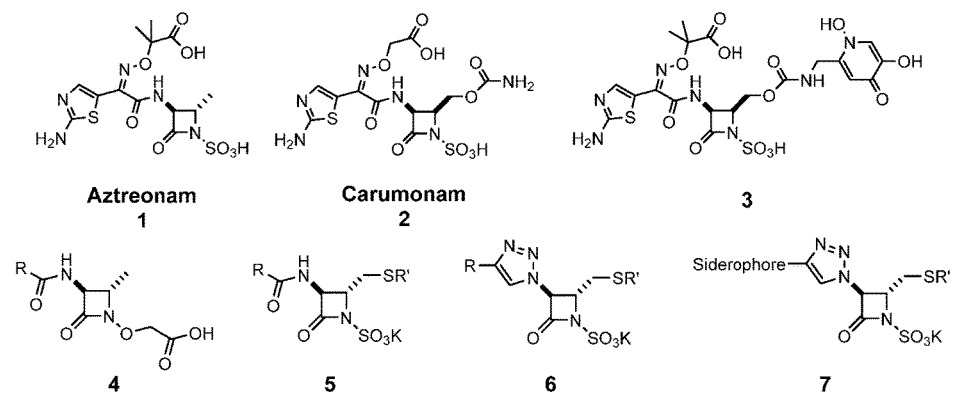
FIG. 1. Examples of synthetic monobactams: aztreonam (1), which shows potent and specific activity against Gram-negative bacteria and high β-lactamase stability, and carumonam (2).

Research has resulted in the synthesis of several promising antibacterial compounds. Relevant examples are aztreonam (1, FIG. 1) (which shows potent and specific activity against Gram-negative bacteria and high β-lactamase stability) and Carumonam (2, FIG. 1). Another example is represented by the oxamazin class of monocyclic heteroatom activated β-lactams (4, FIG. 1) which show good biological activity against Gram-negative bacteria.

Copper(I)-catalyzed 1,2,3-triazole formation is a powerful reaction which has found numerous applications in drug discovery and in the labelling of biomolecules. Although the 1,2,3-triazole moiety is not present in nature, numerous synthetic molecules containing this functionality display interesting biological activity (antibacterial, herbicidal, fungicidal, antiallergenic and anti-HIV). Because of their bioisosterism with peptide bonds and participation in hydrogen bonding, 1,2,3-triazoles are useful linkers. They are also stable to metabolic degradation (unlike amides they do not undergo hydrolysis and unlike benzenoids and related aromatic heterocycles they do not undergo oxidation or reduction). Numerous groups have reported the synthesis of β-lactams containing a triazole moiety but there are only a few examples in which the β-lactam is conjugated to different molecular fragments using a triazole at the C3 position as the linker. For example, Vatmurge et. al reported the Cu(I)-catalyzed cycloaddition reaction of azido β-lactams and terminal alkynes derived from cholic acid and deoxycholic acid.

The syntheses of monocyclic β-lactams of general structure 5 and 6 which display a sulfur-containing functionality at the C4 position and/or a 1,2,3-triazole moiety at the C3 position is of interest. The triazole moiety was considered because of its bioisosterism with peptide bonds and its ability to form hydrogen bonds with biomolecular targets and also because it could be used as a linker between the β-lactam and an iron-chelating moiety.

In 1987, the synthesis of functionalized β-lactam 11 (Scheme 1) starting from the commercially available vinylacetic acid was reported. The key step of the synthesis was the bromine-induced cyclization of protected hydroxamic acid. Herein is described further functionalization of the β-lactam core 11.

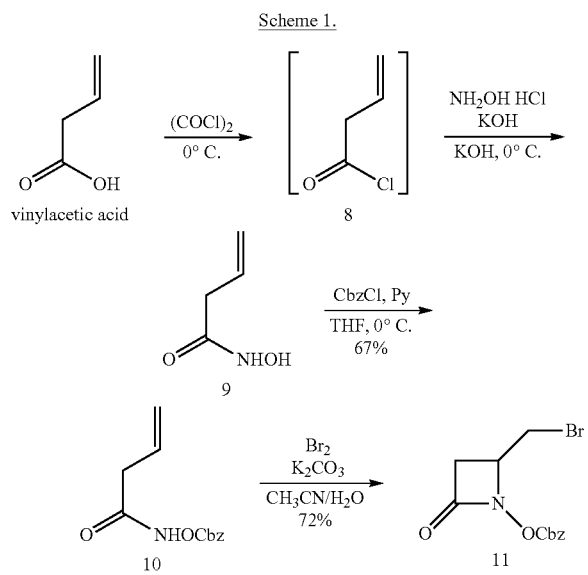

It was envisaged that the β-lactam core 11 could be elaborated into the fully functionalized compounds with generalized structure 5 using the synthetic strategy shown in Scheme 2. Starting from compound 11, nucleophilic substitution with a thiol would give compound 12 which would be elaborated into N-tosyloxy β-lactam 13 using a deprotection-protection sequence.

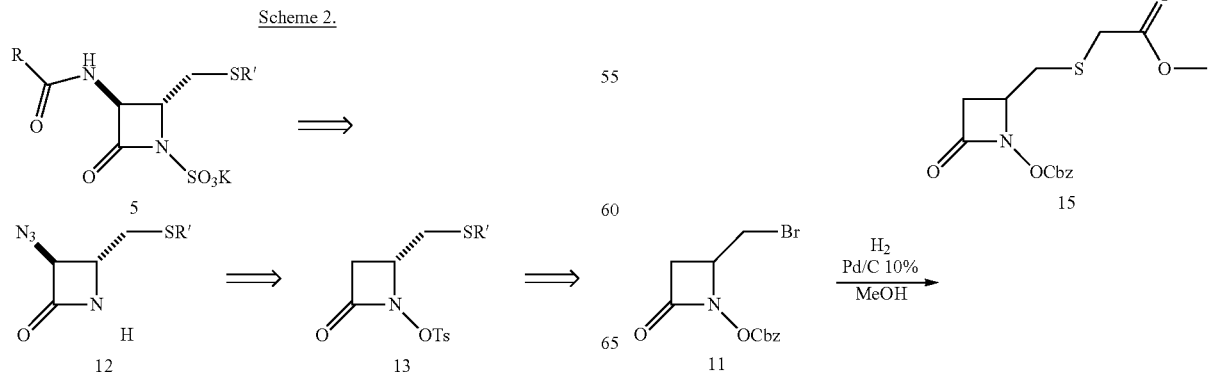

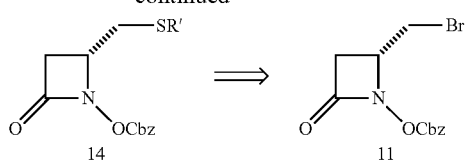

The introduction of an acylamino side chain at the C3 position would be accomplished using methodology previously developed in the group. It was reported that the reaction of an N-tosyloxy β-lactam with different nucleophiles led to products in which the nucleophile had added at the C3 position of the ring and the N—O bond had been cleaved. This reaction could be used for the introduction of an azido group at the C3 position of the β-lactam 13 (Scheme 2). Finally, reduction of the azide followed by acylation would create the final compound 5.

The present disclosure begins with β-lactam 11. Described herein are studies towards the further functionalization of β-lactam 11 to N-sulfonyloxy β-lactam 13.

The reaction of 11 with methyl thioglycolate, under basic conditions, met with failure due to lability of the Cbz group under the reaction conditions (Scheme 3). It was therefore decided to switch the Cbz group to a more stable protecting group, namely a benzyl group.

Catalytic hydrogenation gave N-hydroxy β-lactam 16 which was not isolated but was directly treated with benzyl bromide and potassium carbonate to create the desired compound 17 (Scheme 3). Reaction of 17 with methyl thioglycolate under basic conditions created the substitution product 18 in high yield but, unfortunately, the increased stability of the benzyl group also resulted in the impossibility of its removal from the product. The use of different reaction conditions (catalytic hydrogenation, TMSI, Lewis acids, Birch reduction conditions) resulted either in decomposition or recovery of the starting material.

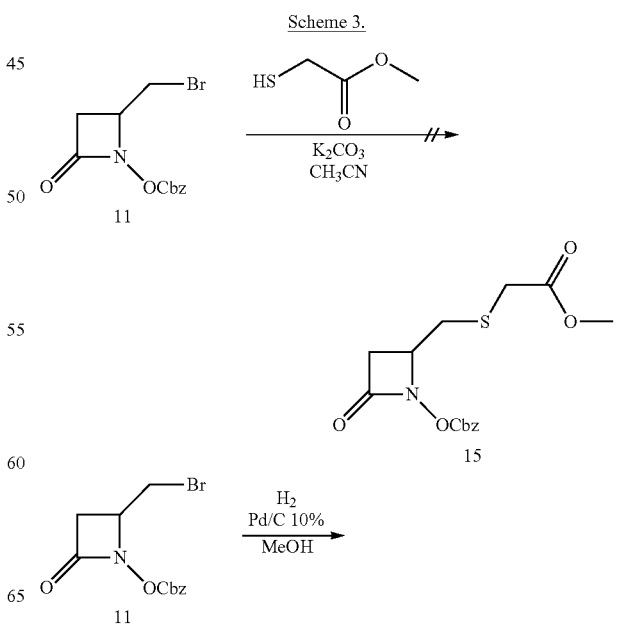

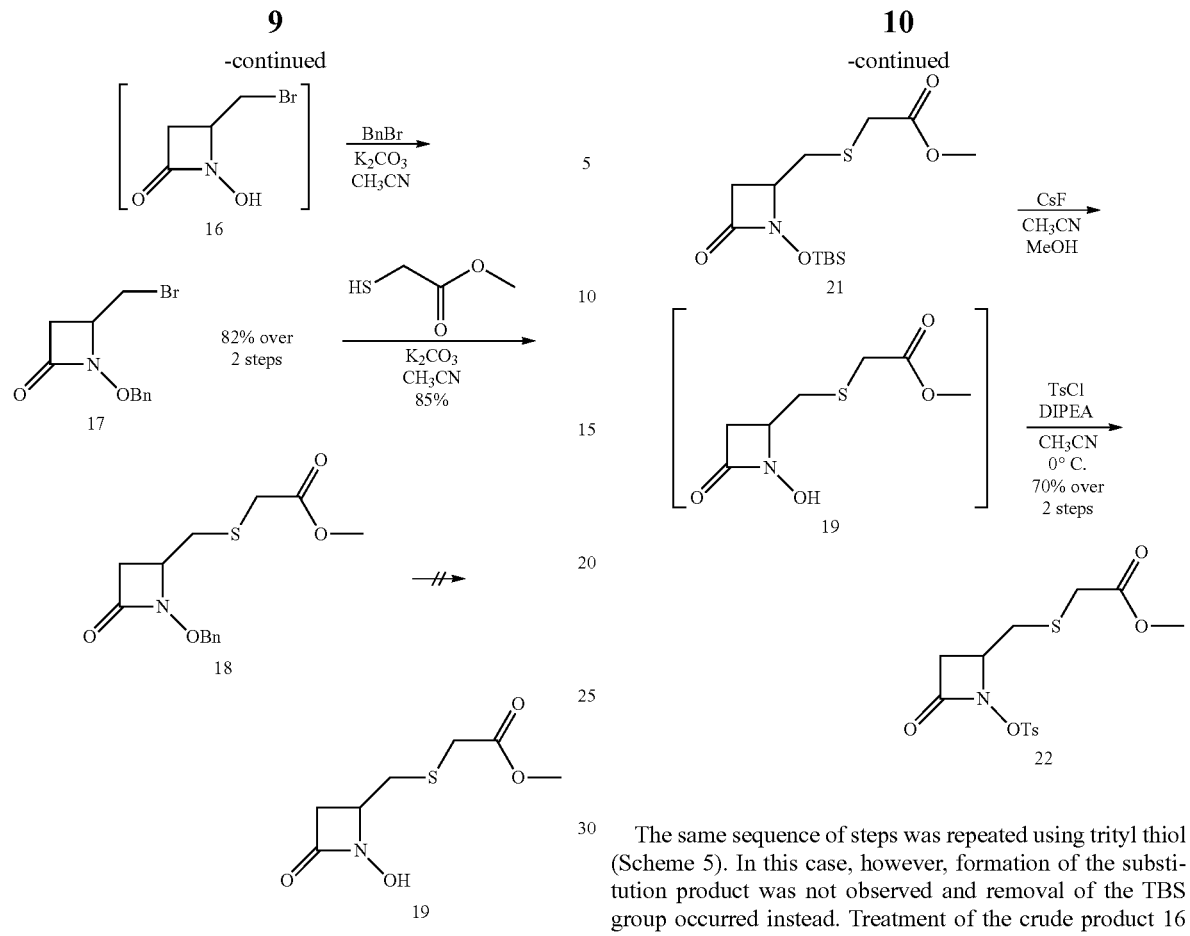

The use of a TBS group was then envisaged. Catalytic hydrogenation of 11 followed by reaction of the resulting N-hydroxy β-lactam with TBSCl and Et₃N in DCM afforded the desired compound 20 in 69% yield over 2 steps (Scheme 4). Then reaction of β-lactam 20 with methyl thioglycolate under basic conditions, created the desired product 21 in moderate yield (it was observed that the yield decreased with prolonged reaction time). Removal of the TBS group was then accomplished by treatment of compound 21 with an excess of CsF in a mixture of CH₃CN and MeOH and the resulting N-hydroxy β-lactam was treated with TsCl under basic conditions to afford N-tosyloxy β-lactam 22 in 70% yield over 2 steps.

The same sequence of steps was repeated using trityl thiol (Scheme 5). In this case, however, formation of the substitution product was not observed and removal of the TBS group occurred instead. Treatment of the crude product 16 with TBSCl and Et₃N in DCM led to isolation of the starting material 20. This result led to the conclusion that the TBS group was not stable enough under the reaction conditions.

Scheme 5.

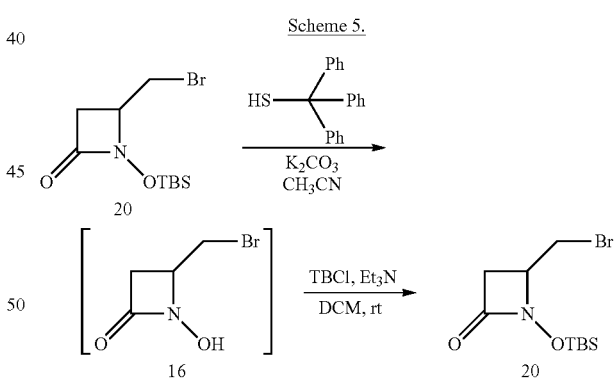

The use of an allyl group, which could be removed using palladium chemistry, was then attempted. Catalytic hydrogenation of 11 afforded the desired N-hydroxy β-lactam which was not purified but directly treated with allyl bromide under basic conditions. The resulting β-lactam 23 underwent reaction with methyl thioglycolate to afford the desired substituted β-lactam 24a in high yield. Nucleophilic substitution on β-lactam 23 was also performed with a variety of thiols in order to prove the generality of the method. In all cases, the desired products 24b-e were obtained in moderate to good yield, even after a prolonged reaction time (Table 1).

Scheme 4.

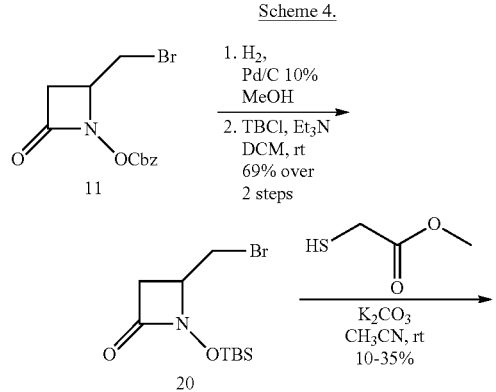

Scheme 6.

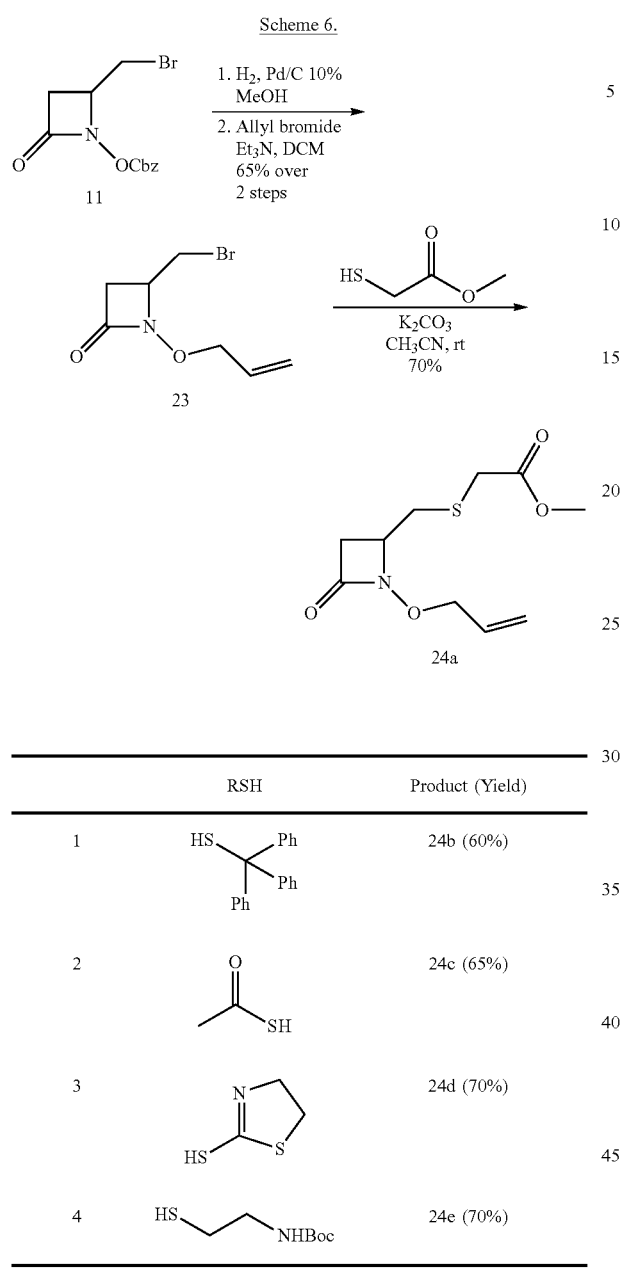

Starting from β-lactam 24a, the allyl group could be removed using palladium chemistry (Scheme 7). The resulting N-hydroxy β-lactam was not isolated but was treated with TsCl and DIPEA in CH$_3$CN to N-tosyloxy β-lactam 22. Under these conditions, however, compound 22 could only partially purified. The compound was reacted with TMSN$_3$ and DIPEA in CH$_3$CN to give the desired compound (±)-25 in 71% yield over 3 steps, a single diastereoisomer. Although the $^1$H NMR signals for CH(3) and CH(4) were not fully resolved and it was not possible to obtain their coupling constant, it was assumed initially that 25 had the trans configuration, consistent with previous results.

Scheme 7.

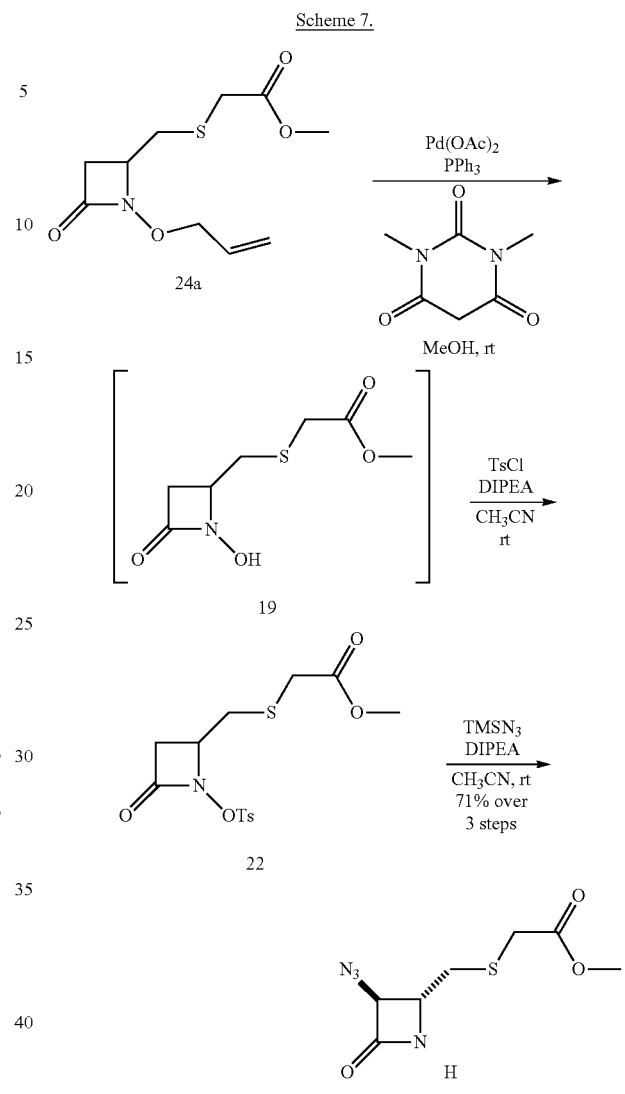

β-Lactam (±)-25 was further elaborated using the steps shown in Scheme 8. Reduction of the azide followed by reaction of the resulting amine with phenylacetyl chloride afforded compound (±)-27 in moderate yield. Treatment of (±)-27 with an excess of SO$_3$.DMF complex gave N-sulfonated β-lactam (±)-28 as the tetrabutylammonium salt. At this point, it was possible to determine the coupling constant (J=2.8 Hz) between CH(3) and CH(4) in the $^1$H NMR spectra. This result was, indeed, consistent with the trans configuration of the substituents on the β-lactam ring. Finally, ion exchange on Dowex resin (50WX8, K$^+$ form) afforded the final compound (±)-29 as the potassium salt suitable for antibacterial assays. Again, the $^1$H NMR of the final compound was consistent with the trans configuration of the substituents at the C(3) and C(4) positions (J=3.0 Hz).

Scheme 8.

Scheme 9.

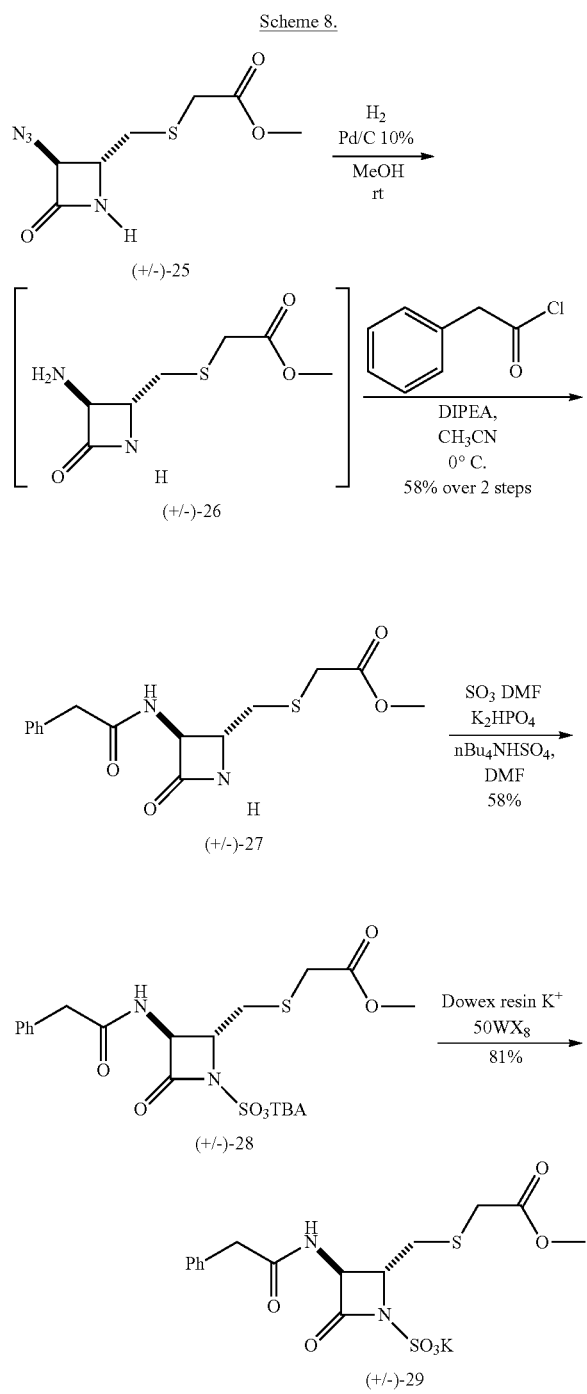

The same sequence of steps was used to introduce an aminothiazole methoxime (ATMO) side chain at the C3 position of the β-lactam (Scheme 9). The azide functionality in β-lactam (±)-25 was again reduced via catalytic hydrogenation and the resulting amine (±)-26 underwent reaction with NHS ester 30 in DMF, at room temperature, afforded the desired compound 31 in moderate yield. Sulfonation, followed by ion exchange on Dowex resin, afforded the desired β-lactam 32 in moderate yield.

Figure 2:
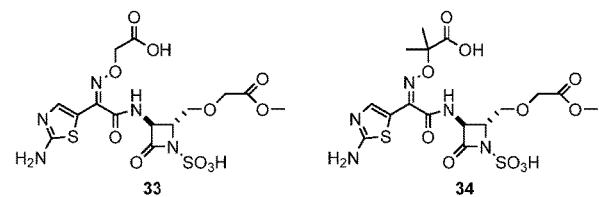
FIG. 2. β-lactams 33 and 34 showing different ATMO side chains at the C3 position.

The same synthetic route can be used for the introduction of different ATMO side chains at the C3 position of the β-lactam (e.g. structures 33, 34, FIG. 2).

Having defined the synthetic route for the full elaboration of the β-lactam core 24a, the compatibility of the process with protected amine derivative 24e was tested using similar steps but introducing an aminothiazole methoxime (ATMO) side chain, a simplified form of the more extended ATMO side chain of the important antibiotic aztreonam, at the C(3) position.

Starting from amino ethanethiol derivative, 24e, removal of the allyl protecting group was again followed by reaction of the resulting N-hydroxy β-lactam with tosyl chloride (Scheme 10). The resulting N-tosyloxy β-lactam 36 was partially purified by column chromatography on silica gel and reacted with TMSN$_3$ under basic conditions to give the azide containing, N-unsubstituted β-lactam (±)-37 in moderate overall yield. Again, the product was a single diastereoisomer (racemic mixture) and the coupling constant between CH(3) and CH(4) indicated the trans relationship of the substituents (J=2.0 Hz). Hydrogenolysis of the azide produced the corresponding amine (±)-38 which was then treated with an excess of NHS ester 30 in DMF at 70° C. to give the product 39, with the desired side chain. At this stage, the ¹H NMR signals for CH(3) and CH(4) also were fully resolved and they were consistent with the trans relationship of the substituents (CH(3) doublet with J=2.3 Hz and CH(4) doublet of doublets with J=2.3, 6.3, 6.3 Hz). Finally, sulfonation of 39 with an excess of SO₃.DMF complex afforded the mono-sulfonated compound 40 in modest yield. All the analytical data were consistent with the structure of the mono-sulfonated compound in which the sulfonation took place on the β-lactam nitrogen and not the relatively non-nucleophilic amine substituent of the ATMO moiety.

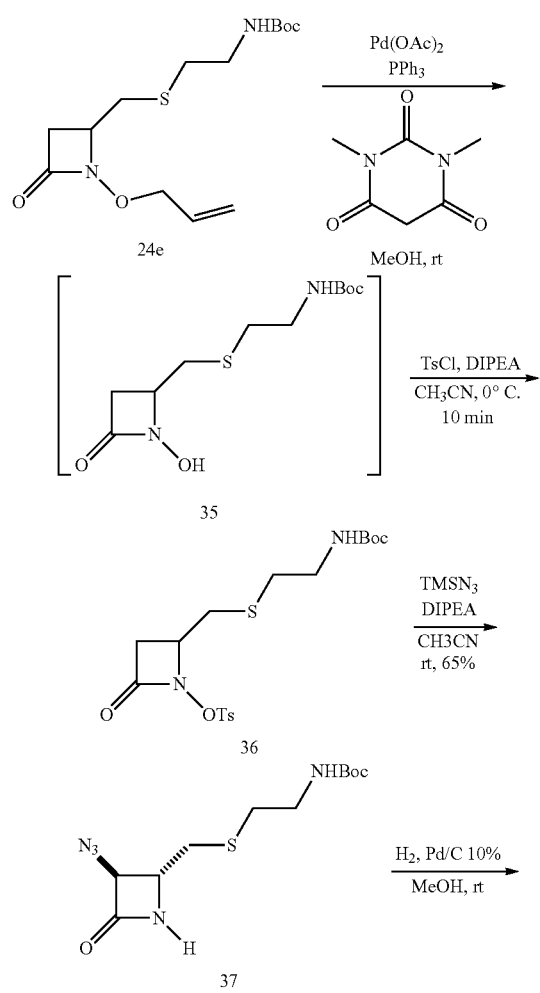

Scheme 10.

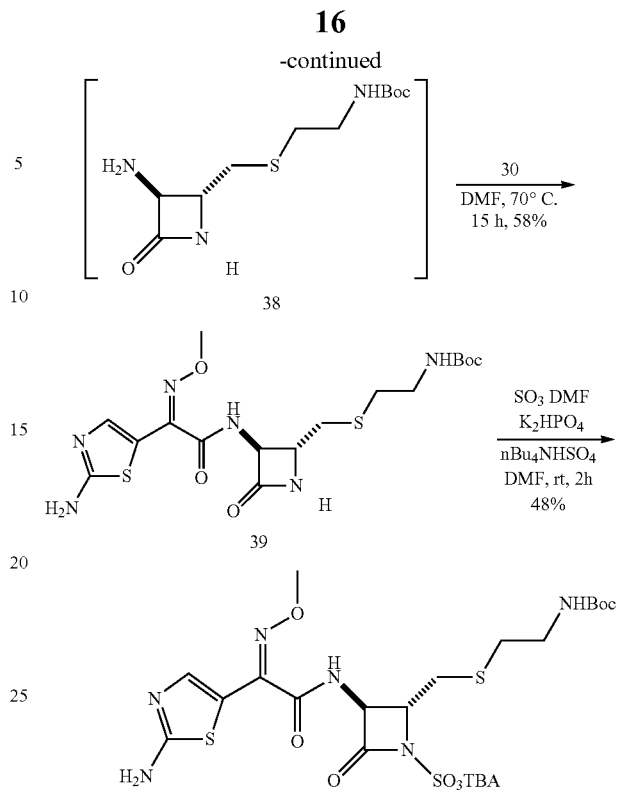

To confirm the sulfation selectivity, the synthesis was repeated with an alternative route, as shown in Scheme 11. Reduction of the azide group in (±)-37 again gave amine (±)-38 which reacted with FmocCl under basic conditions to give β-lactam (±)-41 in moderate yield (Scheme 11). Reaction of (±)-41 with an excess of SO₃.DMF complex afforded the mono-sulfonated compound (±)-42, as the tetrabutylammonium salt. Then removal of the Fmoc protecting group under basic conditions, followed by reaction of the crude amine with NHS ester 30, gave (±)-40 which was identical to the previously obtained mono-sulfonated compound in Scheme 10. Ion exchange on Dowex resin (K⁺ form, 50WX8) in H₂O/THF afforded potassium salt, (±)-43. Subsequent removal of the Boc group gave the corresponding free amine (±)-44.

Scheme 11.

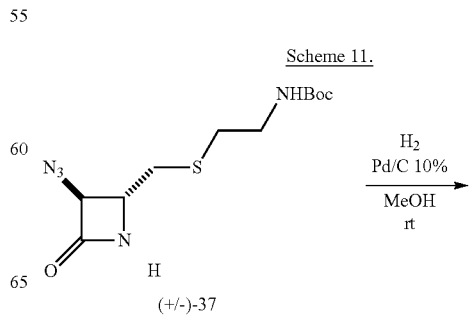

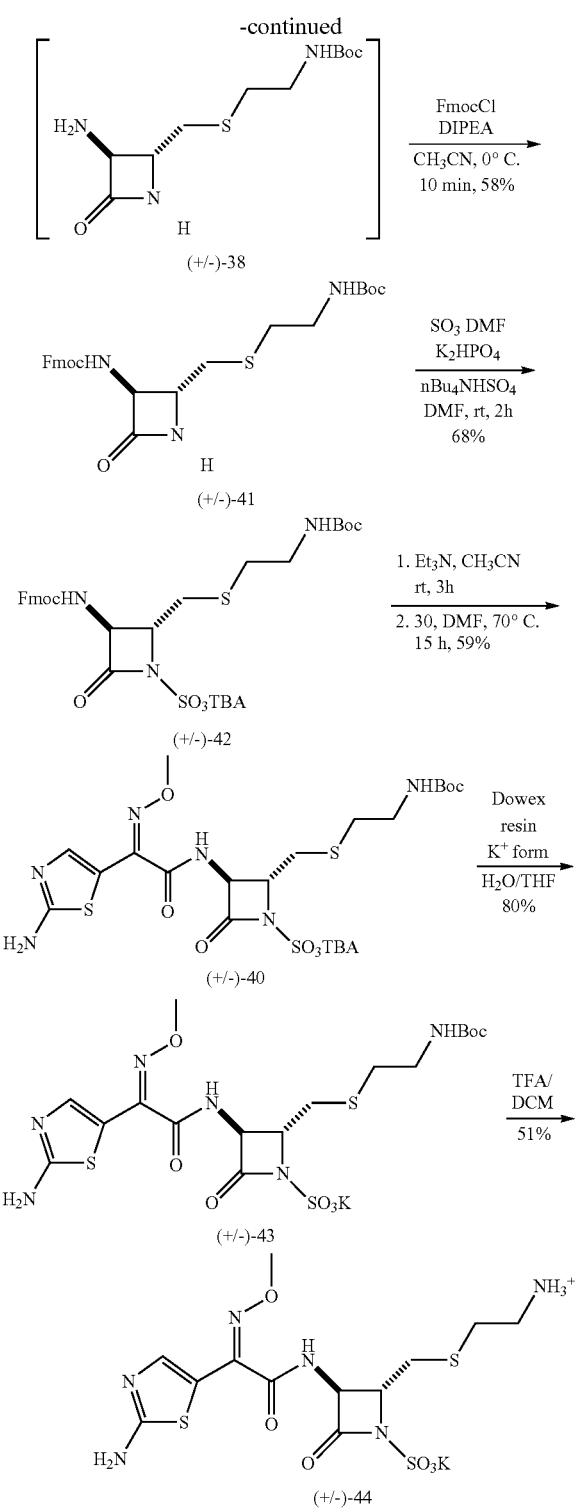

the final compound (±)-48. In the $^1$H NMR of compound (±)-47 it was observed that the coupling constant between protons at the C3 and C4 positions (J=3.0 Hz) is consistent with the trans configuration of the substituents at these positions.

Scheme 12.

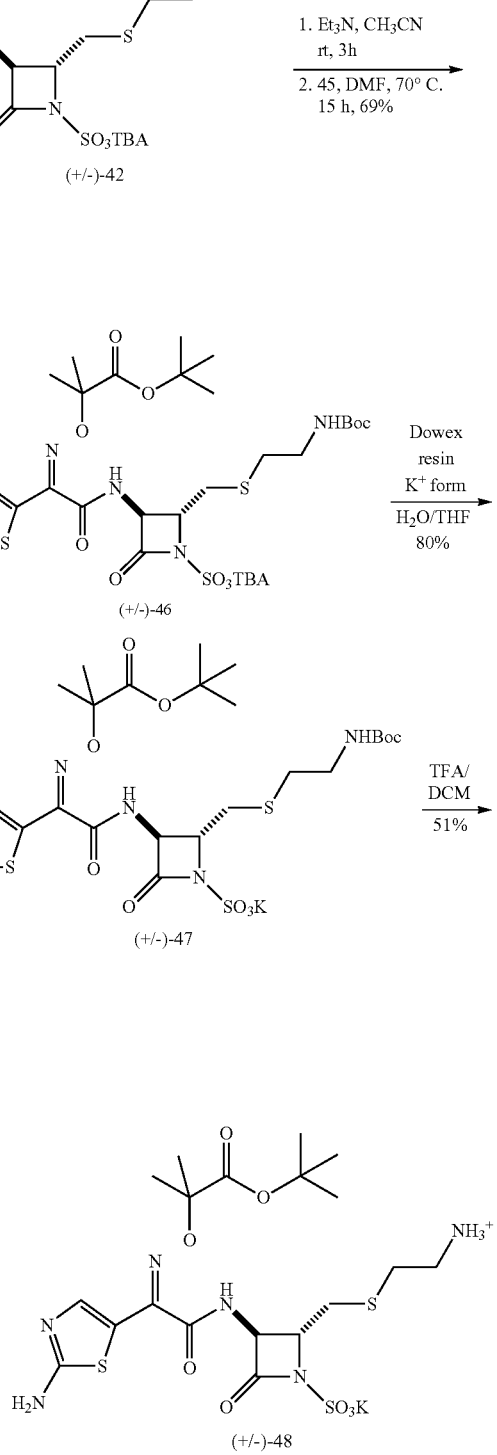

The same route was repeated using a different ATMO side chain (45) (Scheme 12). Starting from compound (±)-42, the Fmoc protecting group was removed under basic conditions and the resulting amine was reacted with NHS ester 45 in DMF at 70° C. The coupling product (±)-46 could be purified by column chromatography and it was obtained in moderate yield. Then ion exchange on (±)-46 gave compound (±)-47 as the potassium salt. Finally, treatment of (±)-47 with an excess of trifluoroacetic acid (TFA) afforded

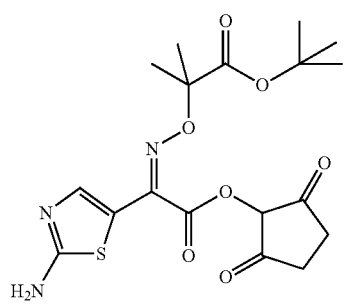

Initial studies directed toward the introduction of a sulfur-containing heterocycle at the position C4 of the β-lactam were also performed. Reaction between β-lactam 23 and 2-mercaptothiazoline in $CH_3CN$, under basic conditions, afforded the substitution product 24d in moderate yield (Table 1). Then the allyl protecting group was removed using palladium chemistry and the resulting N-hydroxy β-lactam underwent reaction with tosyl chloride and DIPEA to give N-tosyloxy β-lactam 50 (Scheme 13). Reaction of 50 with $TMSN_3$ and DIPEA afforded the desired product (±)-51 in moderate yield, as a single diastereoisomer (racemic mixture).

Scheme 13.

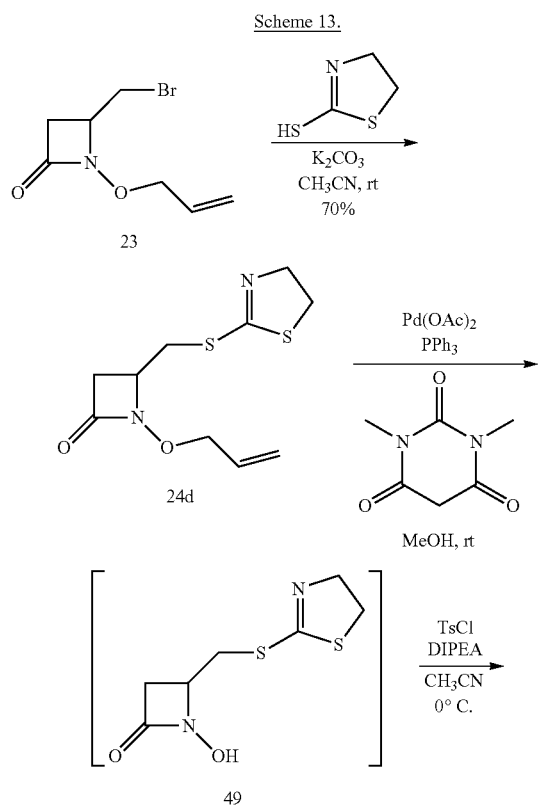

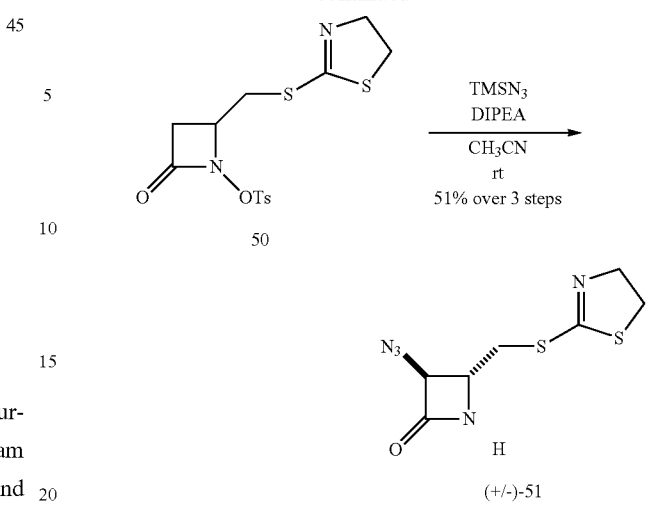

Catalytic hydrogenation did not afford the reduced compound 52. Various reduction methods can be attempted (e.g. $PPh_3$). Reduction of the azide to the corresponding amino group can be followed by the synthetic steps as previously described (acylation, sulfonation and ion exchange, Scheme 14).

Scheme 14.

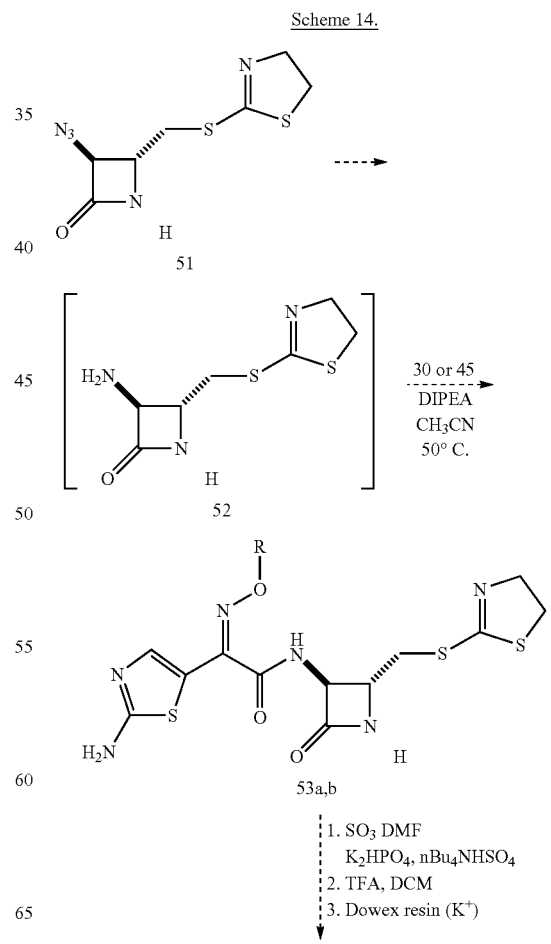

-continued

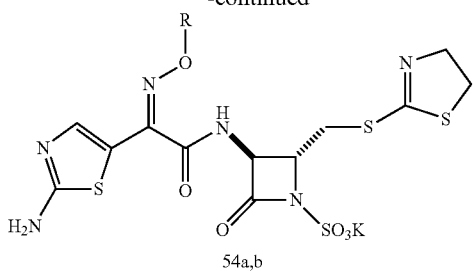

54a,b

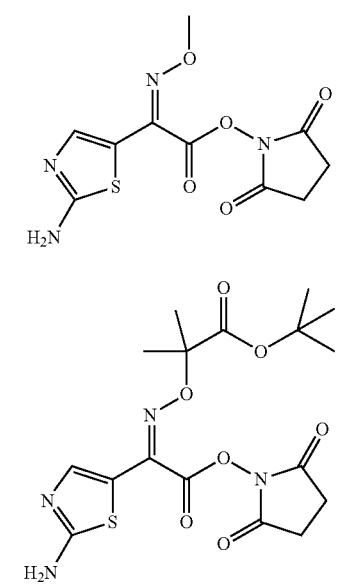

a. R = Me
b. R =

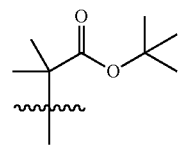

Click chemistry was used for the development of a library of compounds containing a 1,2,3-triazole moiety at that position. A Cu(I)-catalyzed cycloaddition reaction of β-lactam (±)-25 with ethyl propiolate afforded the desired compound (±)-55 in 78% yield (Scheme 15). The sulfonation, followed by ion exchange, gave the final compound (±)-56 in 70% yield.

Scheme 15.

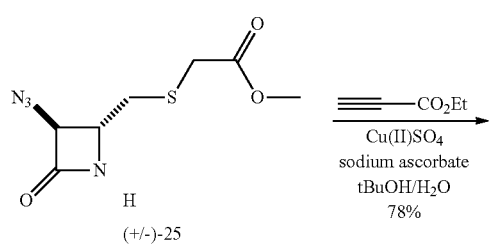

-continued

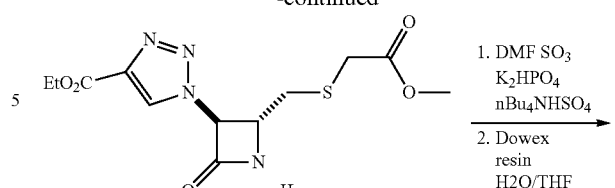

(+/-)-55

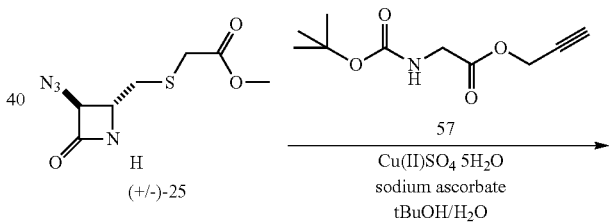

(+/-)-56

The reaction of β-lactam (±)-25 with the glycine-derived alkyne (±)-58 was also performed (Scheme 16): the desired compound (±)-58 was obtained in good yield (75%).

Scheme 16.

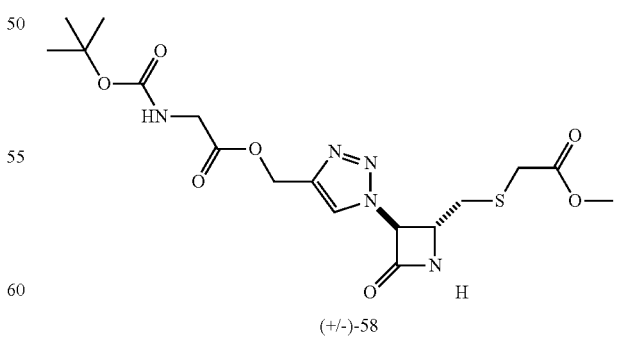

(+/-)-58

β-Lactam (±)-58 was also converted to final compound (±)-59 in two steps: sulfonation and ion exchange (Scheme 17).

Scheme 17.
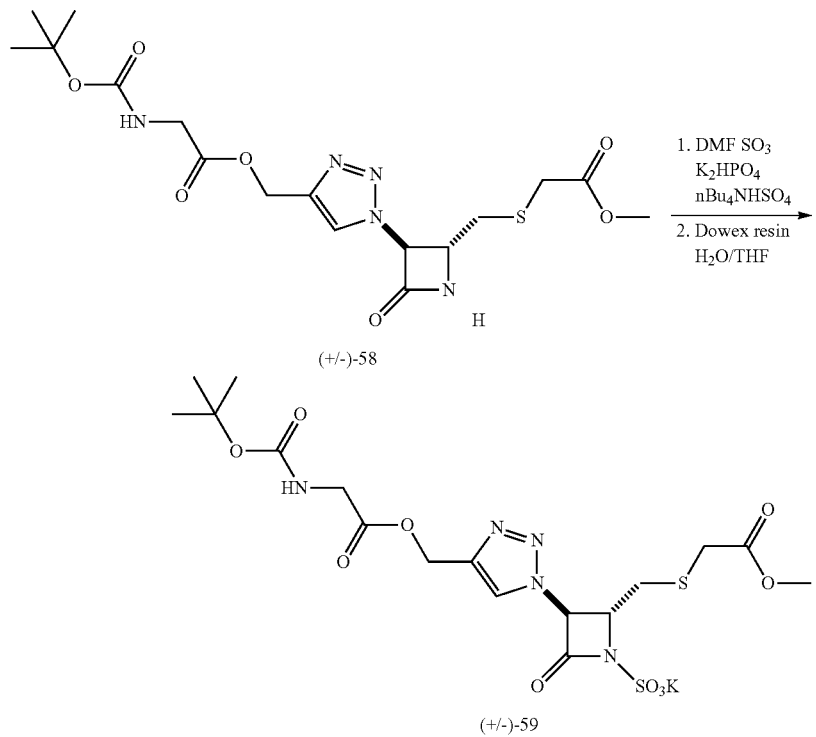
Compound (±)-59 was of particular interest because removal of the Boc protecting group could allow the linkage of the β-lactam with an iron-chelating moiety, through amide bond formation (Scheme 18).
Scheme 18.
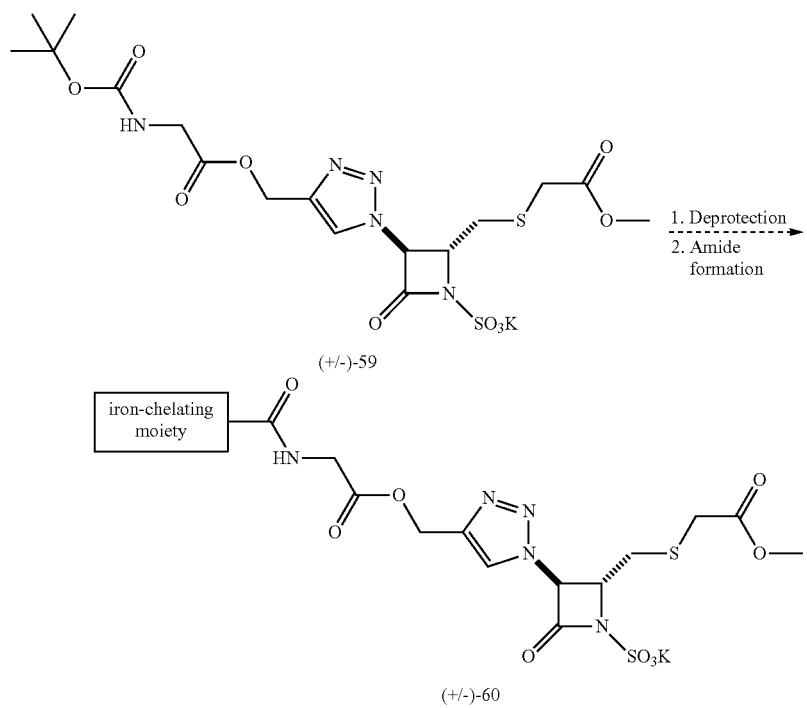

In order to expand the library of compounds available for testing, β-lactam 11 was converted in a variety of N-sulfonyloxy 3-lactams 61a,h using a two steps sequence: catalytic hydrogenation followed by reaction of the resulting N-hydroxy β-lactam with a sulfonyl chloride, under basic conditions (Scheme 19).

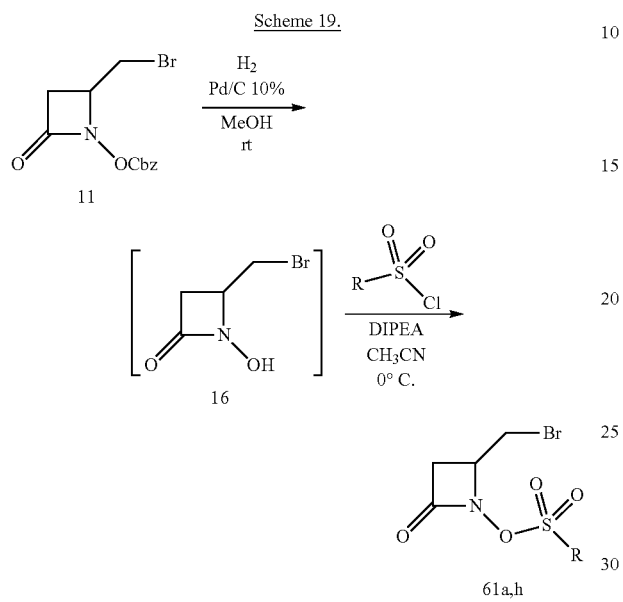

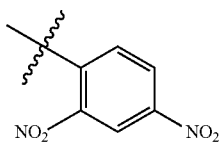
f

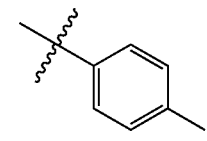
g

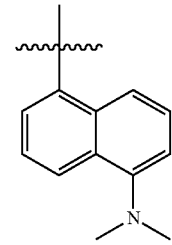
h

All intermediates and the final compounds were tested for antibacterial activity using agar diffusion essays (Table 2). The N-sulfonyloxy β-lactams 61a-h displayed moderate activity against Gram-positive bacteria.

N-sulfonyloxy β-lactam 65 was also synthesized using the synthetic route displayed in Scheme 20. N-sulfonyloxy β-lactam 65 synthesized by this method did not have any activity.

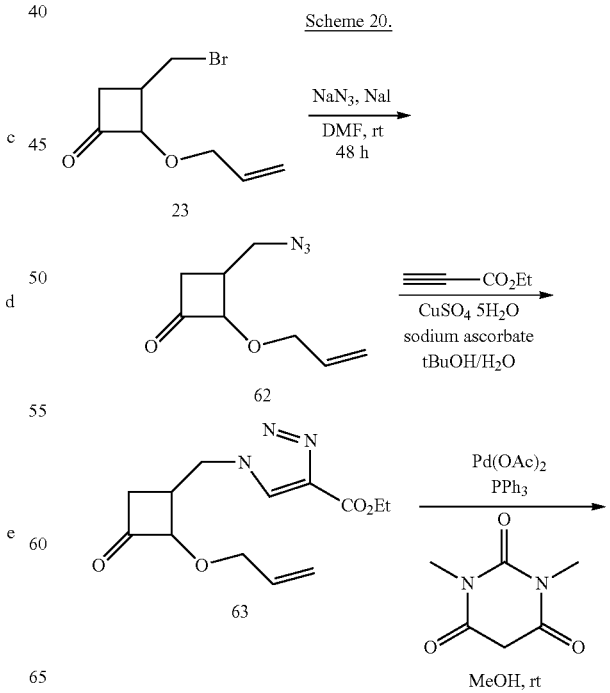

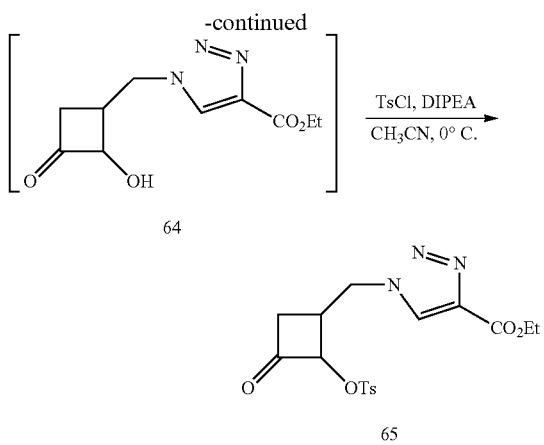

Azide-containing β-lactam 62 can also be elaborated using click chemistry (Scheme 21). Reaction of 62 with a variety of alkynes gives products of general structure 66 which can be further elaborated in three steps: deprotection using palladium chemistry, reaction of the resulting N-hydroxy β-lactam with benzyl bromoacetate and cataslytic hydrogenation.

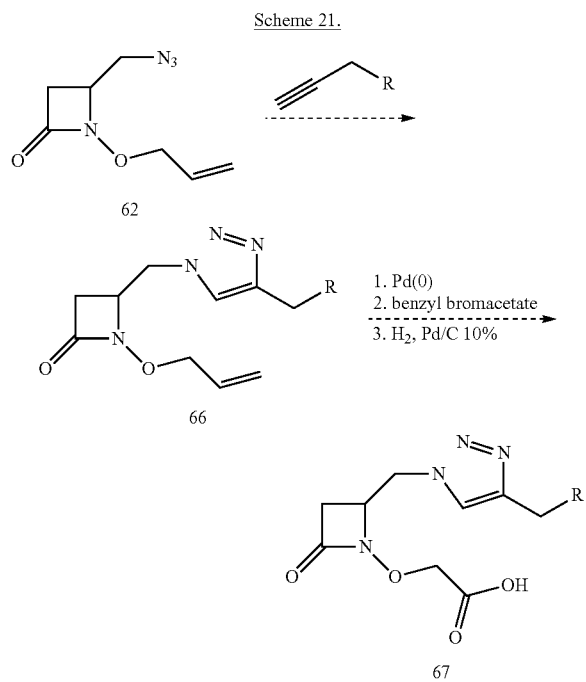

Methodologies for the synthesis of novel monocyclic β-lactams containing either a sulfur-containing functionality or a 1,2,3-triazole moiety at the C4 position have been described herein. A skilled artisan will appreciate that the same methodologies can be used for the synthesis of β-lactams displaying a 1,2,3-triazole at the C3 position.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into subranges as discussed above. In the same manner, all ratios recited herein also include all sub ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated.

A "subject" or "patient" as understood herein is an animal, particularly a mammal. A subject in need of treatment or, particularly, in need of the compounds described herein, is an animal or mammal which can be treated by the compounds described herein. In some cases, a subject in need of treatment has a bacterial infection. The bacterial infection can be an infection of a Gram-positive bacterium, including but not limited to *B. subtilis* and *M. vaccae*; or with a Gram-negative bacterium, including but not limited to *A. baumannii, P. aeruginosa* and *E. coli.*

Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

With respect to chemical synthesis, an "effective amount" refers to an amount effective to bring about a recited effect, such as an amount necessary to form products in a reaction mixture.

Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

Specific values listed below for radicals, substituents, and ranges, are for illustration only; they do not exclude other defined values or other values within defined ranges for radicals and substituents. Generic terms include each of their species. For example, the term halo includes and can explicitly be fluoro, chloro, bromo, or iodo.

The term "alkyl" refers to a branched, unbranched, or cyclic hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 15 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or optionally substituted, for example, with a substituent described below. The alkyl can also be optionally partially or fully unsaturated. As such, the recitation of an alkyl group can optionally include both alkenyl or alkynyl groups, in certain embodiments. The alkyl can be a monovalent hydrocarbon radical, as described and exemplified above, or it can be a divalent hydrocarbon radical (i.e., an alkylene), depending on the context of its use.

The term "alkoxy" refers to the group alkyl-O—, where alkyl is as defined herein. Examples of alkoxy groups include, but are not limited to, methoxy, ethoxy, n-propoxy, isopropoxy, n-butoxy, tert-butoxy, sec-butoxy, n-pentoxy, n-hexoxy, 1,2-dimethylbutoxy, and the like. The alkoxy can be unsubstituted or substituted.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 20 carbon atoms, for example, about 6-10 carbon atoms, in the cyclic skeleton. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

An alkyl, alkoxy, or aryl group can be the group R, or the group R can be an alkyl, alkoxy, or aryl moiety linked to the core structure or formula by a linker or linking group. A "linker" or "linking group" refers to an organic or inorganic chain or moiety that connects to other groups of a molecule. A linker can be, for example, a group L where L is a an alkylene, an alkenylene, an aryl diradical, a direct bond or a divalent radical of the formula —W—Z—W—; where each W is independently —N(R')C(=O)—, —C(=O)N(R')—, —OC(=O)—, —C(=O)O—, —O—, —S—, —S(O)—, —S(O)2-, —N(R')—, —C(=O)—, —(CH2)n- where n is 1-3, —(CX*2)-, —(CH2)n-(CX*2)- where n is 1-3, or a direct bond; and Z is a divalent moiety selected from (C1-C12)alkyl, (C2-C12)alkenyl, (C2-C12)alkynyl, (C3-C8)cycloalkyl, (C6-C10)aryl, —N(R')C(=O)—, —C(=O)N(R')—, —OC(=O)—, —C(=O)O—, —N(R')—, —C(=O)—, —(CX*2)-, —(CH2)n-(CX*2)- where n is 1-3, —(OCH2-CH2)n- where n is 1 to about 10, —C(O)NH(CH2)n- where n is 1 to about 6, —OP(O)(OH)O—, —OP(O)(OH)O(CH2)n- where n is 1 to about 6, —OP(O)(OH)OCH2CH(OH)CH2-, —N+(Me)2(CH2)n- where n is 1 to about 6; or (C1-C12)alkyl, (C2-C12)alkenyl, (C2-C12)alkynyl, or —(OCH2-CH2)n- optionally interrupted between two carbons, or between a carbon and an oxygen, with a (C3-C8)cycloalkyl, heteroaryl, heterocycle, or (C6-C10)aryl group, where n is 1 to about 6; or Z is a direct bond.

The term "substituted" indicates that one or more (e.g., 1, 2, 3, 4, or 5; in some embodiments 1, 2, or 3; and in other embodiments 1 or 2) hydrogen atoms on the group indicated in the expression using "substituted" is replaced with a "substituent". The substituent (e.g., when a group is "optionally substituted") can be one of a selection of the indicated group(s), or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano, as well as the moieties illustrated in the schemes and Figures of this disclosure, and combinations thereof. Additionally, suitable substituent groups can be, e.g., —X, —R, —O—, —OR, —SR, —S—, —NR2, —NR3, =NR, —CX3, —CN, —OCN, —SCN, —N=C=O, —NCS, —NO, —NO2, =N2, —N3, NC(=O)R, —C(=O)R, —C(=O)NRR, —S(=O)2O—, —S(=O)2OH, —S(=O)2R, —OS(=O)2OR, —S(=O)2NHR, —S(=O)R, —OP(=O)(OR)2, —P(=O)(OR)2, —OP(=O)(OH)(OR), —P(=O)(OH)(OR), —P(=O)(O—)2, -5 P(=O)(OH)2, —C(=O)R, —C(=O)X, —C(S)R, —C(O)OR, —C(O)O—, —C(S)OR, —C(O)SR, —C(S)SR, —C(O)NRR, —C(=S)NRR, —C(=NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group.

The term "solvate" refers to a solid compound that has one or more solvent molecules associated with its solid structure. Solvates can form when a solid compound is crystallized from a solvent, wherein one or more solvent molecules become an integral part of the solid crystalline matrix. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. A hydrate is a specific type of a solvate. Hydrates can form when a compound is solidified or crystallized in water, wherein one or more water molecules become an integral part of the solid crystalline matrix. The compounds of the formulas described herein can be hydrates.

General Synthetic Methods

Preparation of the compounds described herein can be prepared according to the methods described herein, or may be prepared according to known techniques in the art of organic synthesis. Many linking groups for conjugating substituents to the compounds described herein are commercially available, and/or can be prepared as described in the art. Information regarding general synthetic methods that may be used to prepare the compounds described herein, particularly with respect employing linking groups, may be found in Greg T. Hermanson, *Bioconjugate Techniques*, Academic Press, San Diego, Calif. (1996). Useful linkers and conjugation techniques are further described by Roosenberg et al., *Curr. Med. Chem.* 2000, 7, 159; Wittmann et al., *Bioorg. Med. Chem.* 2002, 10, 1659; and Heinisch et al., *J. Med. Chem.* 2002, 45, 3032. Additional useful reactions well known to those of skill in the art are referenced in March's *Advanced Organic Chemistry Reactions, Mechanisms, and Structure,* 5th Ed. by Michael B. Smith and Jerry March, John Wiley & Sons, Publishers; and Wuts et al. (1999), 5 *Protective Groups in Organic Synthesis,* 3rd Ed., John Wiley & Sons, Publishers.

The methods of preparing compounds of the invention can produce isomers in certain instances. Although the methods of the invention do not always require separation of these isomers, such separation may be accomplished, if desired, by methods known in the art. For example, preparative high performance liquid chromatography methods may be used for isomer purification, for example, by using a column with a chiral packing.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate.

Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like. Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can bedissolved or dispersed at effective levels, optionally with the aid of non-toxic surfactants.

Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user. Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician. The compound can be conveniently administered in a unit dosage form, for example, containing 5 to 1000 mg/m$_2$, conveniently 10 to 750 mg/m$_2$, most conveniently, 50 to 500 mg/m$_2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods of treating a bacterial infection in a mammal, which involve administering to a mammal having a bacterial infection an effective amount of a compound or composition described herein. A mammal includes a primate, human, rodent, canine, feline, bovine, ovine, equine, swine, caprine, bovine and the like.

The ability of a compound of the invention to treat a bacterial infection may be determined by using assays well known to the art. For example, the design of treatment protocols, toxicity evaluation, data analysis, quantification of cell kill and inhibition and the biological significance of the use of antibacterial screens are known.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1, Thiol Products

The bromine atom in compound 9 was displaced by a variety of thiols to give the desired products 11a-e in moderate to good yields (Table 1.1).

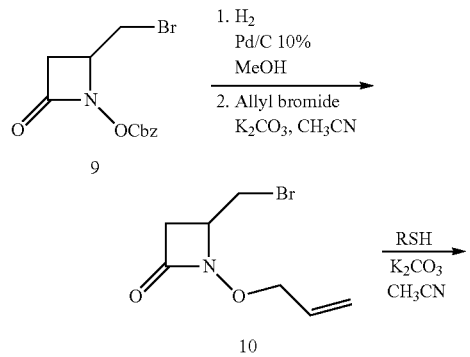

-continued

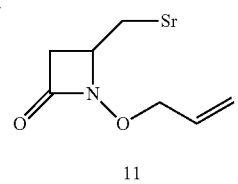

TABLE 1.1

| Thiol | | Yield (%) |
|---|---|---|
| HS-CH$_2$-C(O)-O-CH$_3$ | 11a | 70 |
| CH$_3$-C(O)-SH | 11b | 65 |
| Ph$_3$C-SH | 11c | 60 |
| HS-CH$_2$CH$_2$-NHBoc | 11d | 79 |
| HS-thiazoline | 11e | 70 |

The instability of the Cbz group under the basic conditions of the nucleophilic substitution reaction required a deprotection-protection sequence (9 to 10, Scheme 1.1).

Example 2. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| Compound X | 100.0 |
| Lactose | 77.5 |
| Croscarmellose sodium | 15.0 |
| Microcrystalline cellulose | 92.5 |
| Magnesium stearate | 3.0 |
| Total | 300.0 |

| (ii) Tablet 2 | mg/tablet |
|---|---|
| Compound X | 20.0 |
| Microcrystalline cellulose | 410.0 |
| Starch | 50.0 |
| Sodium starch glycolate | 15.0 |
| Magnesium Stearate | 5.0 |
| Total | 500.0 |

| (iii) Capsule | mg/capsule |
|---|---|
| Compound X | 10.0 |
| Colloidal silicon dioxide | 1.5 |

-continued

| | |
|---|---|
| Lactose | 465.5 |
| Pregelatinized starch | 120.0 |
| Magnesium stearate | 3.0 |
| Total | 600.0 |

| (iv) Injection 1 (1 mg/ml) | mg/ml |
|---|---|
| Compound X (free acid form) | 1.0 |
| Dibasic sodium phosphate | 12.0 |
| Monobasic sodium phosphate | 0.7 |
| Sodium chloride | 4.5 |
| 1.0N sodium hydroxide solution (pH adjustment to 7.0-7.5) | q.s. |
| water for injection | q.s. ad 1 mL |

| (v) Injection 2 (10 mg/ml) | mg/ml |
|---|---|
| Compound X (free acid form) | 10.0 |
| Monobasic sodium phosphate | 0.3 |
| Dibasic sodium phosphate | 1.1 |
| Polyethylene glycol 400 | 200.0 |
| 0.1N sodium hydroxide solution (pH adjustment to 7.0-7.5) | q.s. |
| Water for injection | q.s. ad 1 mL |

| (vi) Aerosol | mg/can |
|---|---|
| Compound X | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| Compound X | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical gel 2 | wt. % |
|---|---|
| Compound X | 5% |
| Methylcellulose | 2% |
| Methyl paraben | 0.2% |
| Propyl paraben | 0.02% |
| Purified water | q.s. to 100 g |

| (ix) Topical ointment | wt. % |
|---|---|
| Compound X | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical cream 1 | wt % |
|---|---|
| Compound X | 5% |
| White beeswax | 10% |
| Liquid paraffin | 30% |
| Benzyl alcohol | 5% |
| Purified water | q.s. to 100 g |

| (xi) Topical cream 2 | wt. % |
|---|---|
| Compound X | 5% |
| Stearic acid | 10% |
| Glyceryl monostearate | 3% |
| Polyoxyeythlene stearyl ether | 3% |
| Sorbitol | 5% |
| Isopropyl palmitate | 2% |
| Methyl paraben | 0.2% |
| Purified water | q.s. to 100 g |

Example 3. General Experimental Methods

Unless otherwise indicated, chemicals and solvents were from commercial suppliers and were used as received. All of the solvents were of analytical grade or were distilled prior to use. Dichloromethane ($CH_2Cl_2$) and acetonitrile ($CH_3CN$) were distilled from $CaH_2$. Tetrahydrofuran (THF) was distilled from a mixture of sodium metal and benzophenone ketyl. Dimethylformamide (DMF) and diisopropylethylamine (DIPEA) were used from Acros Seal anhydrous bottles. $^1H$ NMR and $^{13}C$ NMR spectra were obtained on a 500 MHz Bruker spectrometer and FIDs were processed using ACD/SpecManager version 11. Chemical shifts (δ) are given in parts per million (ppm) and are referenced to residual solvent peaks as internal standards. Coupling constants (J) are reported in Hertz (Hz). High resolution, accurate mass measurements were obtained with a Bruker micrOTOF II electrospray ionization time-of-flight mass spectrometer in positive mode. Infrared spectra were recorded with a ThermoNicolet IR 200 Spectrometer and reported as $cm^{-1}$. All reactions were conducted under Argon atmosphere unless otherwise noted. Solvents were removed in vacuo on a rotary evaporator. Reactions were monitored by thin layer chromatography (TLC) performed with aluminum-backed Merck 60-F254 silica gel plates using a 254 nm lamp, ceric ammonium molybdate (CAM) stain, $FeCl_3$ stain, $KMnO_4$ stain or ninhydrin stain for visualization. Silica gel chromatography was performed using Sorbent Technologies silica gel 60 (32-63 μm). Melting points were determined in capillary tubes using a Thomas Hoover melting point apparatus and are uncorrected.

All liquids and media were sterilized by autoclaving (121° C., 15 min) before use. All aqueous solutions and media were prepared using distilled, deionized and filtered water (Millipore Milli-Q Advantage A10 Water Purification System). Luria broth (LB) was purchased from VWR. Mueller-Hinton No. 2 broth (MHII broth; cation adjusted) was purchased from Sigma-Aldrich. McFarland $BaSO_4$ turbidity standards were purchased from bioMérieux, Inc. Sterile plastic petri dishes (145 mm×20 mm; Greiner Bio-One) were purchased from VWR. Ciprofloxacin was purchased from Sigma-Aldrich.

The enzymes KPC-2, Oxa-48, AmpC and NDM-1 were purchased from Emerald Bioscience and the enzymes CTX-14 and SHV-12 were expressed and purified from E. coli at Rempex pharmaceutical (San Diego, Calif.).

Example 4. Biological Activity of β-Lactams

Compounds described herein were tested for antibiotic activity against a variety of bacteria, according to the methods described herein and below.

Antibacterial activity of the compounds was determined by a modified Kirby-Bauer[27-28] agar-diffusion assay. Overnight cultures of test organisms were grown in LB broth for 18-24h and standard suspensions of $1.5 \times 10^6$ CFU/mL were prepared in saline solution (0.9% NaCl) according to a 0.5 $BaSO_4$ McFarland Standard. This standardized suspension (0.1 mL) was added to 34 mL of sterile, Mueller Hinton No. 2 agar tempered to 47-50° C. After gentle mixing, the inoculated agar media was poured into a sterile plastic petri dish (145 mm×20 mm) and allowed to solidify near a flame with the lid cracked for 30 min. Wells of 9.0 mm diameter were cut from the petri dish agar and filled with exactly 50 μL of the test sample solution. For studies using mixtures of compounds, both test compounds were diluted to equal concentrations and 50 μL of the mixed compound solution was added to the cut well. The petri dish was incubated at 37° C. for 18-24 h and the inhibition zone diameters were measured (mm) with an electronic caliper after 24-48 h.

All compound-containing solutions were prepared by first making a 20 mM solution of the compound in DMSO and then diluting that solution 10-fold with MeOH to give the final 2 mM solution used in the assay.

Plates were incubated after inoculation at 37° C. for 20 hours. Plates were photographed after 1 day. *M. vaccae* required a longer incubation time, 48 hours, and was photographed after 3 days.

The results of these experiments are shown in Table 2.

The MICs for compounds 41, 43 and 44 were determined against the same panel of Gram-positive and Gram-negative bacteria: all values were >50 μM.

Compound 48 displayed very interesting activity on Gram-negative bacteria and on the Gram-positive *M. luteus*.

As shown in Table 2, compounds 61a-h showed weak antibacterial activity against Gram-positive bacteria but they were not active against Gram-negative bacteria.

TABLE 2

Spectrum of antimicrobial activity in the Agar Diffusion Assay.
Biological Activity

| | | | | | | | Zone of Growth Inhibition (mm) | | | |
|---|---|---|---|---|---|---|---|---|---|---|
| | B. Subtilis ATCC | S. Aureus | M. Luteus ATCC | M. Vaccae IMET | A. Baumannii ATCC | B. Dolosa AU | P. Aeruginosa | | E. Coli | |
| | 6633 | SG511 | 10240 | 10670 | 17961 | 0018 | K799/wt | K799/61 | DC0 | DC2 |
| 41 | 13P | 0 | 0 | 17V | 13P | 0 | 15P | 16P | 15V | 0 |
| 43 | 18 | 0 | 0 | 0 | 0 | 0 | 0ppt | 16/24P | 0 | 29 |
| 44 | 16V | 0 | 14s | 0 | 15/18P | 0 | 0 | 14 | 23 | 20/24P |
| 48 | 0 | 0 | 26P | 0 | 12P | 15 | 18P | 31/36P | 26 | 28 |
| 61a | 15* | 22*P | 17 | 31P** | 0 | 0 | 0 | 0 | 0 | 0 |
| 61b | 12 | 14P | 13.5P* | 16V* | 0 | 0 | 0 | 0 | 0 | 0 |
| 61c | 12/15P | 15 | 16P* | 19V* | 0 | 0 | 0 | 0 | 0 | 0 |
| 61d | 21P* | 15V* | 20V* | 19P* | 0 | 0 | 0 | 0 | 0 | 0 |
| 61e | 13*V | 0 | 0 | 0 | 0 | 0 | 0 | 12.6* | 0 | 0 |
| 61f | 22 | 21P | 18P | 28 | 16V | 0 | 0 | 0 | 0 | 16P |
| 61g | 0 | 18V | 16P | 19V | 13.5 | 0 | 0 | 0 | 0 | 0 |
| 61h | 12/17P | 15* | 18V* | 19V* | 0 | 0 | 0 | 0 | 0 | 0 |

P: Indicates unclear inhibition zone.
V: Indicates a very unclear inhibition zone.
*Indicates a slightly misshapen zone . . . most likely to solubility issues.

The synthesis of a series of N-sulfonated β-lactams 61a-h, which display weak antibacterial activity against Gram-positive bacteria, was previously reported. These compounds were included as positive controls for the current experiments.

The sulfamates, 43 and 44, and their synthetic intermediates were tested against a panel of Gram-positive and Gram-negative bacteria (Table 2) using Kirby-Bauer agar diffusion assays. As previously stated, the 3-phenylacetamido β-lactam 29 did not show any activity. Interestingly, intermediate 41 displayed moderate activity against tested Gram-positive bacteria, *B. subtilis* and *M. vaccae*, and representative Gram-negative bacteria, *A. baumannii, P. aeruginosa* and *E. coli*. In the case of *P. aeruginosa*, the compound showed activity against both the wild type (K799/0 wt) and the permeability mutant (K799/61) in which the integrity of the bacterial cell wall is compromised. In the case of *E. coli*, the compound was only active against the permeability mutant DC0. Interestingly Boc protected compound 43 had moderate activity against *B. subtilis* and the permeability mutant forms of *P. aeruginosa* and *E. coli*. The inactivity against the corresponding wild strains is probably due to the inability of the compound to penetrate the bacterial cell wall.

Free amine, 44, obtained by removal of the Boc group from 43, was also moderately active against *B. subtilis* and *M. luteus* and *A. baumannii* and the permeability mutant strains of *P. aeruginosa* and *E. coli*. However, it was also active against the wild type *E. coli* DC2, indicating that the zwitterionic nature of the compound allowed it to permeate that bacterial cell wall.

Example 5. In Vitro Activity of β-Lactams

Compounds described herein were tested for inhibitory activity against β-lactamase enzymes, according to the methods described below.

To the first row of a 2-mL deep 96-well block was added 1 mL of 50 mM sodium phosphate buffer at pH 7 with 0.1 mg/mL BSA (bovine serum albumin). To the first row was added an appropriate amount of a 10 mg/mL solution of the compound to be tested to make a 640 μM (4×) solution. Each of the other wells in the 96-well block were charged with 750 μL of the aforementioned buffer. The rows were then repeatedly diluted 1:3 so that the final concentrations of the individual 96-well plates would range in concentrations from 160 μM to 3 nM (8 dilutions). The master block was then used to add 50 pt to each corresponding well in the 96-well flat-bottom plate. An additional 50 of buffer was added to each well. Once the plates were prepared, 50 μL of the enzyme to be tested against were added in buffer to each well [KPC-2 (0.147 mg/mL), CTX-M-14 (0.102 mg/mL), Oxa-14 (0.331 mg/mL), AmpC (0.699 mg/mL), SHV-12 (0.111 mg/mL), NDM-1 (0.110 mg/mL)]. The plates were incubated at rt for 10 min before 50 μL. of an appropriate indicator were added to each well and the optical density at 495 nm was measured over time. For each enzyme, other than NDM-1, nitrocefin was used. Nitrocefin (10 μM for SHV-12, 50 μM for the other enzymes), was appropriate because when cleaved by a β-lactamase, the color changes from yellow to red. For NDM-1, imipenem (10 μM) was the indicator of choice. Rather than observe the growing presence of optical density at 495 nm, as with nitrocefin, the disappearance of imipenem was monitored. The inhibition curves were monitored and used to perform enzyme kinetics according to Waley to determine the Ki (μM) of each compound against the β-lactamases screened.

The results of these experiments are shown in Table 3.

TABLE 3

Ki values for compounds 61b, c, a, d against selected β-lactamase enzymes from classes A, B, C and D.

| | | | | Ki (μM) | | | |
|---|---|---|---|---|---|---|---|
| | | | | Enzyme | | | |
| KPC-2 | CTX-M-14 | Oxa-48 | AmpC | SHV-12 | PAM 2035 | NDM-1 | VIM-1 |
| | | | Class | | | | |
| A | A | D | C | A | C | B | B |
| 61b >160 | >160 | 4.673 | >160 | 0.198 | >160 | >160 | N/A |
| 61c >160 | >160 | >160 | >160 | 0.190 | >160 | >160 | >160 |
| 61a 19.290 | 0.149 | 1.481 | >160 | 0.779 | >160 | >160 | >160 |
| 61d >160 | >160 | >160 | >160 | >160 | >160 | >160 | N/A |

Compounds 61a-d were also tested for β-lactamase inhibitory activity against selected enzymes from classes A, B, C and D (Ambler classification). Also in this case an unusual selectivity was observed (Table 3): while compound 61c was active only against the class A enzyme SHV-12, compounds 61a,b inhibited enzymes from both classes A and D. Although there are two β-lactamase inactivators that show activity against both classes A and C of β-lactamases (the penem BRL 42715 and tazobactam), there are no examples of clinically used inhibitors of both classes A and D. Also worth noting is the activity of 61a,b against the class D enzyme Oxa-48, which is particularly relevant for its notable carbapenem-hydrolyzing activity and its resistance to the clinically used β-lactamase inhibitors clavulanic acid, sulbactam and tazobactam.

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An N-sulfonyloxy β-lactam compound of Formula (I):

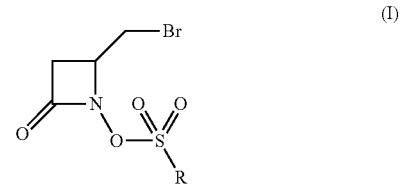

wherein R is an optionally substituted aryl with the proviso that R is not tolyl, or an optionally substituted alkenyl(aryl), and the bromine is optionally replaced by a sulfur-containing side chain; and Formula (I) has an optional aminothiazole methoxime (ATMO) containing side chain at C3.

2. The compound of claim 1 wherein R is selected from the group consisting of:

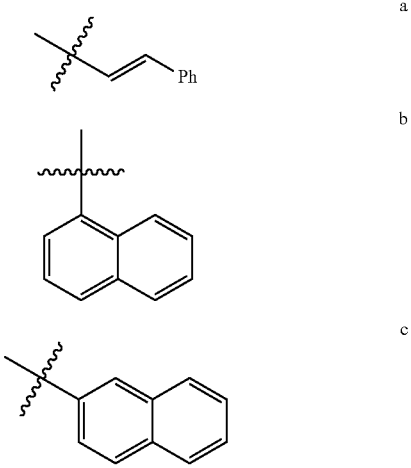

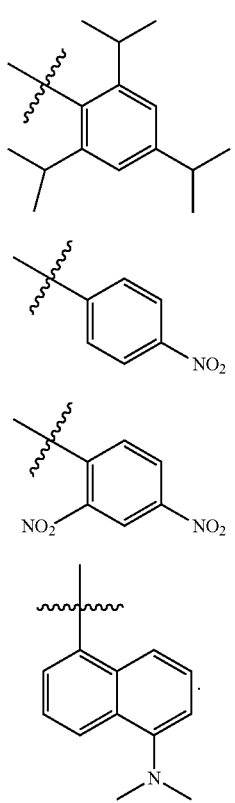

3. A compound selected from the group consisting of 41, 43, 44, and 48, or a pharmaceutically acceptable salt thereof:

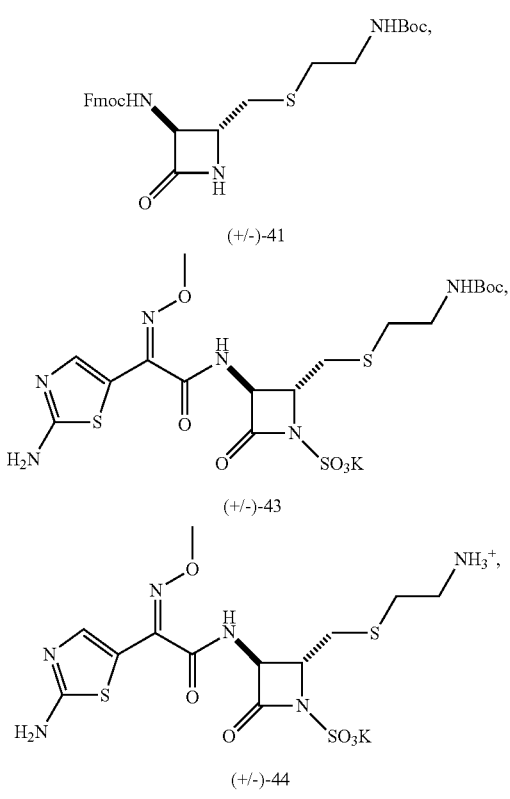

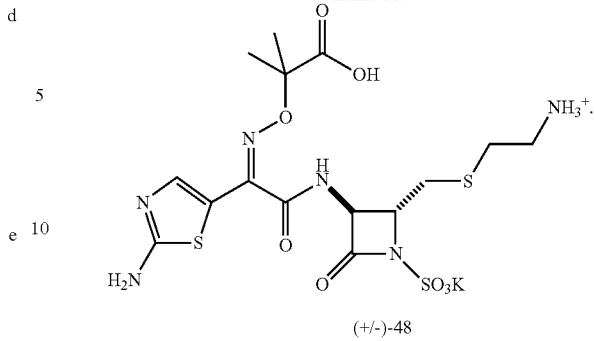

4. The compound of claim 1 wherein the bromine moiety of Formula (I) is replaced with a sulfur-containing side chain.

5. The compound of claim 1 wherein Formula (I) has an aminothiazole methoxime (ATMO) containing side chain at the C3 position.

6. A method of inhibiting β-lactamase activity comprising contacting a β-lactamase enzyme with a compound of claim 1.

7. The method of claim 6, wherein the β-lactamase enzyme is a β-lactamase enzyme isolated from a pathogenic bacterium.

8. The method of claim 6, wherein the β-lactamase enzyme is naturally occurring in a pathogenic bacterium.

9. The method of claim 8, wherein the pathogenic bacterium is selected from the group consisting of gram positive bacteria and gram negative bacteria.

10. A method of inhibiting β-lactamase activity comprising contacting an N-sulfonyloxy β-lactam of claim 1 with a β-lactamase enzyme that is naturally occurring in a pathogenic bacterium selected from the group consisting of gram positive bacteria and gram negative bacteria, wherein the gram positive bacteria are selected from the group consisting of *B. subtilis* and *M. vaccae*.

11. The method of claim 9, wherein the gram negative bacteria are selected from the group consisting of *A. baumannii, P. aeruginosa* and *E. coli*.

12. A method of inhibiting β-lactamase activity comprising contacting a β-lactamase enzyme with a compound of claim 2.

13. A method of treating a bacterial infection comprising administering to a subject in need thereof an effective antibacterial amount of a compound of claim 3, or a pharmaceutically acceptable salt thereof.

14. A method of treating a bacterial infection comprising administering to a subject in need thereof an effective antibacterial amount of a compound of claim 1, or a pharmaceutically acceptable salt thereof.

15. A method of treating a bacterial infection comprising administering to a subject in need thereof an effective antibacterial amount of a compound of claim 2, or a pharmaceutically acceptable salt thereof.

16. A method of treating a bacterial infection comprising administering to a subject in need thereof an effective antibacterial amount of a compound of claim 4, or a pharmaceutically acceptable salt thereof.

17. A method of treating a bacterial infection comprising administering to a subject in need thereof an effective antibacterial amount of a compound of claim 5, or a pharmaceutically acceptable salt thereof.

18. A method of inhibiting β-lactamase activity comprising contacting a β-lactamase enzyme with a compound of claim 3.

19. A method of inhibiting β-lactamase activity comprising contacting a β-lactamase enzyme with a compound of claim 4.

20. A method of inhibiting β-lactamase activity comprising contacting a β-lactamase enzyme with a compound of claim 5.

* * * * *